US00PP30184P2

(12) United States Plant Patent
Bradford et al.

(10) Patent No.: US PP30,184 P2
(45) Date of Patent: Feb. 12, 2019

(54) PLUM TREE NAMED 'PLUMCANDY XIV'

(50) Latin Name: *Prunus salicina*
Varietal Denomination: Plumcandy XIV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/732,742

(22) Filed: Dec. 26, 2017

(51) Int. Cl.
*A01H 5/08* (2018.01)

(52) U.S. Cl.
USPC ..... Plt./184

(58) Field of Classification Search
USPC ..... Plt./180, 184
See application file for complete search history.

(56) References Cited

U.S. PATENT DOCUMENTS

PP18,670 P2 3/2008 Bradford
PP20,892 P2 3/2010 Bradford

*Primary Examiner* — Susan McCormick Ewoldt

(57) ABSTRACT

The present invention relates to a plum tree and more particularly to a new and distinct variety broadly characterized by a medium size, vigorous, hardy, and very productive tree. Being self-unfruitful, the present variety requires cross pollination from another plum or interspecific tree that blooms during the mid to late season, such as 'Plumsweet XV' interspecific tree (U.S. Plant Pat. No. 23,687). The present variety's abundance of blossoms and moderate pollen production entices strong bee activity to facilitate pollination. The fruit matures under the ecological conditions described during the first week of September, with first picking on Sep. 5, 2017. The fruit is uniform, very large in size, nearly black in skin color, clingstone in type, full yellow in flesh color, firm in texture, juicy, and excellent in flavor.

1 Drawing Sheet

Botanical classification: *Prunus salicina.*
Variety denomination: 'PLUMCANDY XIV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XIV'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'Plumsweet VIII' interspecific tree (U.S. Plant Pat. No. 18,670) was crossed by us in this manner. To pollinate this interspecific tree, we selected bouquets from several sources of plum trees without keeping specific written details. Upon reaching maturity the fruit from this plum tree was harvested, and the seeds were removed, cracked, stratified and germinated as a group with the label "H23". They were grown as seedlings on their own root in our greenhouse and upon reaching dormancy transplanted to a cultivated area of our experimental orchard located near Le Grand, Calif. in Merced County (San Joaquin Valley). During the summer of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Plumsweet VIII' (U.S. Plant Pat. No. 18,670) interspecific tree, by being a medium size tree, by blooming in the mid to late season, by being self-unfruitful, and by producing fruit that is oblate in shape, very sweet, juicy, firm, and excellent in flavor, but is distinguished therefrom by being much more productive and by producing fruit that is nearly black instead of greenish red in skin color, that is much larger in size, that is yellow instead of red in flesh color, and that ripens about thirty days later.

The present variety is most similar to 'Blackred XII' (U.S. Plant Pat. No. 20,892) interspecific tree, by being self-unfruitful, by blooming in the mid to late season, by being very productive, and by producing fruit that is nearly black in skin color, that is large in size, that is firm in texture, that is clingstone in type, that is very sweet in flavor, and that matures in mid to late September, but is distinguished therefrom by producing fruit that is yellow instead of pinkish red in flesh color, that is very bumpy instead of smooth on the skin surface, that has more freckling on the skin, and that is much juicier.

SUMMARY OF VARIETY

The present plum variety is characterized by a medium size, vigorous, hardy, and very productive tree. Being self-unfruitful, the present variety requires cross pollination from another plum or interspecific tree that blooms during the mid to late season, such as 'Plumsweet XV' interspecific tree (U.S. Plant Pat. No. 23,687). The present variety's abundance of blossoms and moderate pollen production entices strong bee activity to facilitate pollination. The fruit matures under the ecological conditions described during the first week of September, with first picking on Sep. 5, 2017. The fruit is uniform, very large in size, nearly black in skin color, clingstone in type, full yellow in flesh color, firm in texture, juicy, and excellent in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of full ripe on Sep. 28, 2017, on the original tree during its tenth growing season. All major color code designations are by reference to the Inter-Society Color Council, National Bureau of Standards. Common color names are also used occasionally.

PARENTAGE

Seed parent: 'Plumsweet VIII' (U.S. Plant Pat. No. 18,670) interspecific tree.
Pollen parent: Unknown.

TREE

Size: Medium, reaching and maintaining a height of 10' [3.05 m.] and a spread of 7' [2.13 m.] after ten growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase formed type.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Very productive, thinning usually necessary.
Fertility: Self-unfruitful, requiring cross pollination by a suitable mid to late seasonal blooming plum or interspecific, such as 'Plumsweet XV' interspecific tree (U.S. Plant Pat. No. 23,687).
Bearing: Regular bearer, weather dependent, no crop failures observed as of yet.
Leaf bud burst: Medium, toward the middle of flowering.

Trunk:
- *Size*.—Stocky, reaching a maximum diameter of 4½" [114 mm.] after ten growing seasons.
- *Texture*.—Shaggy.
- *Bark color*.—A Grayish yellowish brown [80. gy.yBr] and Dark grayish brown [62. d.gy.Br] variegation with Strong brown [55. s.Br] crevices present.
- *Lenticels*.—Approximate Number Per Square Inch: 12. Color: Brownish orange [54. brO]. Typical Size: ¼" [6.4 mm.] in length. The width is typically one fourth as much as the length. Shape: Eye-shaped.

Branches:
- *Size*.—Diameter of the scaffold is 3" [76.2 mm.] measured 12" above the crotch, diameter of limb is 1½" [38.1 mm.] measured 12" above the first fork.
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. 2nd Year Wood: Light grayish yellowish brown [79.l.gy.yBr]. Older Wood: A Brownish gray [64. brGy] and Light brown [57. l.Br] variegation.
- *Lenticels*.—Number Per Square Inch: About 30 on second year wood. Color: Strong yellowish brown [74. s.yBr]. Typical size: Small, 1/32" [0.8 mm.] in length. The width is typically one fourth as much as the length. Shape: Eye-shaped.

Leaves:
- *Size*.—Medium to large. Average Length: 4 5/16" [110 mm.]. Average Width: 2" [50.8 mm.].
- *Arrangement*.—Alternate.
- *Thickness*.—Medium.
- *Form*.—Elliptical.
- *Apex*.—Acuminate.
- *Base*.—Acute with an average base angle of seventy-five degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: ½" [12.7 mm.]. Average Thickness: 1/16" [1.6 mm.]. Color: Moderate greenish yellow [102. m.gY] with Grayish reddish orange [39. gy.rO] where exposed to sunlight.
- *Stipules*.—Number: 2 per leaf, up to 6 per growing tip. Average Length: ¼" [6.4 mm.]. Color: Brilliant yellow green [116. brill.YG] becoming Dark grayish reddish brown [47. d.gy.rBr] with age.
- *Glands*.—Number: 2 to 4, most often 2. Position: Usually alternate, positioned on the petiole just below the leaf blade. Form: Globose. Size: Medium, 1/32" [0.8 mm.] in diameter. Color: Moderate greenish yellow [102. m.gY] becoming Dark grayish reddish brown [47. d.gy.rBr] in the center with age.
- *Leaf buds*.—Pointed.

Flower Buds:
- *Hardiness*.—Hardy, with respect to central California blooming season.
- *Diameter*.—Typically 3/16" [4.8 mm.] 1 week before bloom.

*Length*.—Typically 5/16" [7.9 mm.] 1 week before bloom.
*Form*.—Not appressed.
*Surface*.—Slightly pubescent.
*Color*.—White [263. White].

Flowers: Perfect, complete, usually a single pistil, about twenty-two stamens, five sepals and petal locations alternately positioned.
*Average flower diameter*.—1⅛" [28.6 mm.].
*Average flower depth*.—⅜" [9.5 mm.] when fully open.
*Average pedicel length*.—⅜" [9.5 mm.].
*Number of petals*.—Five, no double blossoms observed.
*Petal arrangement*.—Overlapping.
*Petal shape*.—Oval.
*Petal margin*.—Entire, somewhat wavy.
*Average petal diameter*.—½" [12.7 mm.].
*Average petal length*.—9/16" [14.3 mm.].
*Petal apex*.—Rounded.
*Petal base*.—Rounded.
*Petal color*.—White [263. White] on both sides.
*Anther color*.—Pale orange yellow [73. p.OY].
*Pollen production*.—Abundant, bee enticing.
*Pollen color*.—Brilliant yellow [83. brill.Y].
*Stigma color*.—Pale greenish yellow [104. p.gY].
*Stigma position*.—Stigma is located about 1/16" [1.6 mm.] below the average anther position.
*Ovary*.—Non-pubescent.
*Sepal color*.—Brilliant yellow green [116. brill.YG] on both sides.
*Sepal length*.—7/32" [5.6 mm.].
*Sepal width*.—3/16" [4.8 mm.].
*Sepal apex*.—Elliptical to match the width and length.
*Average pistil length*.—9/16" [14.3 mm.].
*Average stamen length*.—½" [12.7 mm.].
*Stamen position*.—Typically located about 1/32" [0.8 mm.] below the petals.
*Ovary*.—Smooth.
*Fragrance*.—Moderate.
*Blooming period*.—Medium to late compared with other varieties, about the same day as 'Blackred XX' plum (U.S. Plant Pat. No. 20,892).
*Onset of bloom*.—One percent on Feb. 17, 2017.
*Date of full bloom*.—Mar. 1, 2017.
*Duration of bloom*.—One to two weeks, dependent on ambient temperature.
*Bloom density*.—Very heavy.
*Number per cluster*.—Typically 2 or 3, up to 6 observed.

FRUIT

Maturity when described: Full ripe, Sep. 28, 2017.
Date of first picking: Sep. 5, 2017.
Date of last picking: Sep. 25, 2017.
Size: Mostly uniform, very large.
*Average diameter axially*.—2 9/16" [65.1 mm.].
*Average diameter across suture plane*.—3⅛" [79.4 mm.].
*Average diameter across cheek plain*.—3⅛" [79.4 mm.].
*Typical weight*.—8.43 ounces [239 grams].
Form: Mostly uniform, symmetrical, oblate.
*Longitudinal section form*.—Oblate.
*Transverse section through diameter*.—Round.
Suture: A shallow trough extending from the base to the apex.
Ventral surface: Rounded.
Lips: Fairly equal.
Cavity: Flaring, circular, suture showing on one side.
*Depth*.—½" [12.7 mm.].
*Breadth*.—1½" [38.1 mm.].
*Stem markings*.—Usually not present.
Base: Truncate, cordate when viewed parallel to the suture.
Apex: Rounded.
Pistil point: An inconspicuous Pale orange yellow [73. p.OY] dot.
Stem: Medium size.
*Average length*.—7/16" [11.1 mm.].
*Average width*.—1/16" [1.6 mm.].
Skin:
*Thickness*.—Medium.
*Surface*.—Very bumpy.
*Tenacity*.—Tenacious to flesh.
*Astringency*.—Slight.
*Tendency to crack*.—None observed.
*Color*.—Purplish black [235. pBlack] throughout with heavy, but very small, Pale orange yellow [73. p.OY] freckling throughout.
*Lenticels*.—Number Per Square Inch: About 100. Average diameter: 1/80" [0.3 mm].
*Bloom*.—Heavy.
Flesh:
*Color*.—A Pale greenish yellow [104. p.gY] smoothly blending to Pale orange yellow [73. p.OY] near the stone with Yellowish white [92. yWhite] fibers close to the stone.
*Surface of pit cavity*.—Covered with Moderate orange yellow [71. m.OY] broken fibers when twisted away from stone.
*Amygdalin*.—Moderate to abundant.
*Juice*.—Abundant, rich.
*Texture*.—Firm, crisp, meaty.
*Fibers*.—Few, fine, tender.
*Ripens*.—Fairly even.
*Flavor*.—A tasty blend of acid and sugar, typically 18 to 21 brix.
*Aroma*.—Wanting.
*Eating quality*.—Excellent.

STONE

Type: Clingstone.
Form: Oval.
Hilum: Narrow.
Base: Cordate.
Apex: Rounded with a very short, sharp tip 1/32" [0.8 mm.] in length.
Sides: Fairly equal.
Surface: Rough throughout.
External color of stone: Light brown [57. l.Br].
Pit wall color when cracked: Moderate yellowish brown [77. m.yBr].
Cavity surface color: Deep yellowish brown [75. deep yBr].
Average pit wall thickness: ⅛" [3.2 mm.].
Average length: 1" [25.4 mm.].
Average width: ¾" [19.1 mm.].
Average breadth: ⅜" [9.5 mm.].
Tendency to split: None observed.

Kernel:

*Form*.—Oval.
*Pellicle color*.—Dark yellowish brown [78. d.yBr].
*Skin color*.—Light brown [57. l.Br].
*Vein color*.—Moderate yellowish brown [77. m.yBr].
*Taste*.—Bitter.
*Viable*.—Yes.
*Average length*.—⅝" [15.9 mm.].
*Average width*.—⅜" [9.5 mm.].

USE

Market: Fresh market and long distance shipping.
Keeping quality: Excellent. Fruit quality observed to remain in good condition after 30 days in standard cold room at 36° Fahrenheit [2° Celsius].
Shipping quality: Excellent.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *prunus salicina*, substantially as illustrated and described, that is most similar to 'Blackred XII' (U.S. Plant Pat. No. 20,892) interspecific tree, by being self-unfruitful, by blooming in the mid to late season, by being very productive, and by producing fruit that is nearly black in skin color, that is large in size, that is firm in texture, that is clingstone in type, that is very sweet in flavor, and that matures in mid to late September, but is distinguished therefrom by producing fruit that is yellow instead of pinkish red in flesh color, that is very bumpy instead of smooth on the skin surface, that has more freckling on the skin, and that is much juicier.

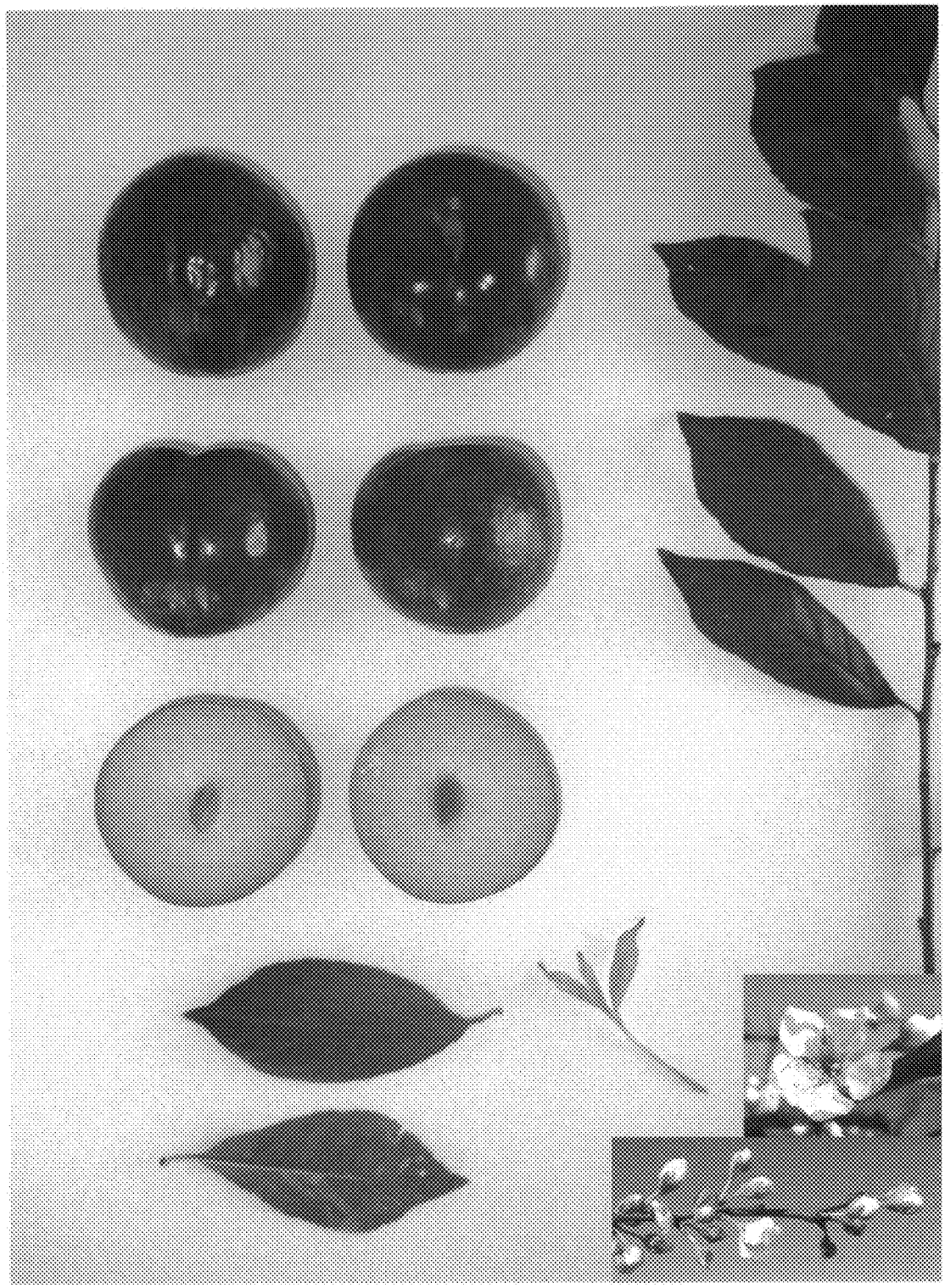

* * * * *